US012642897B2

(12) United States Patent (10) Patent No.: US 12,642,897 B2

Hall et al. (45) Date of Patent: Jun. 2, 2026

(54) ULTRAFILTRATION CONTROL IN EXTRACORPOREAL BLOOD PROCESSING

(71) Applicant: GAMBRO LUNDIA AB, Lund (SE)

(72) Inventors: Henrik Hall, Lund (SE); Björn Ericson, Lund (SE); Roger Nilsson, Höör (SE)

(73) Assignee: Gambro Lundia AB, Lund (SE)

( * ) Notice: Subject to any disclaimer, the term of this patent is extended or adjusted under 35 U.S.C. 154(b) by 632 days.

(21) Appl. No.: 17/911,871

(22) PCT Filed: Feb. 23, 2021

(86) PCT No.: PCT/EP2021/054459
§ 371 (c)(1),
(2) Date: Sep. 15, 2022

(87) PCT Pub. No.: WO2021/185541
PCT Pub. Date: Sep. 23, 2021

(65) Prior Publication Data
US 2023/0310723 A1 Oct. 5, 2023

(30) Foreign Application Priority Data

Mar. 20, 2020 (SE) .................................... 2050308-2

(51) Int. Cl.
*A61M 1/16* (2006.01)
*A61M 1/36* (2006.01)

(52) U.S. Cl.
CPC ........ *A61M 1/1601* (2014.02); *A61M 1/3609* (2014.02); *A61M 2205/3331* (2013.01)

(58) Field of Classification Search
CPC .............. A61M 1/1601; A61M 1/3609; A61M 2205/3331; A61M 1/1613; A61M 1/341;
(Continued)

(56) References Cited

U.S. PATENT DOCUMENTS 8,551,342 B2 10/2013 Moissl et al.
10,449,285 B2 10/2019 Chamney et al.
(Continued)

FOREIGN PATENT DOCUMENTS

WO WO 02053098 A2 7/2002
WO WO 2007109537 A2 9/2007

OTHER PUBLICATIONS

International Search Report from International Patent Application No. PCT/EP2021/054459, mailed May 4, 2021.
(Continued)

*Primary Examiner* — Leslie R Deak
(74) *Attorney, Agent, or Firm* — K&L Gates LLP

(57) ABSTRACT

A control system operates (201) an apparatus for extracorporeal blood processing to extract, process and return the blood of an individual while removing fluid from the blood in accordance with a set value for ultrafiltration rate, UFR. The control system further obtains (202) sensor data representing one or more physiological parameters of the individual, and intermittently performs an optimization procedure (203) to generate the set value based on the sensor data. The optimization procedure comprises: evaluating (203A) the sensor data for detection of a limiting physiological status, LPS, sequentially controlling (203B) the apparatus in accordance with a test sequence of UFRs until the LPS is detected for a current UFR, and updating (203C) the set value based on the current UFR for use in operating the apparatus subsequent to the optimization procedure. The control system may perform a series of temporally separated optimization procedures during a treatment session to adapt the UFR to the individual.

16 Claims, 3 Drawing Sheets

200 — CONTROL METHOD

201 — PERFORM BLOOD PROCESSING INCLUDING UFR GIVEN BY SET VALUE

202 — OBTAIN SENSOR DATA REPRESENTING PHYSIOLOGICAL PARAMETER(S)

203 — UFR OPTIMIZATION PROCEDURE:

203A — EVALUATE SENSOR DATA FOR DETECTION OF LIMITING PHYSIOLOGICAL STATUS, LPS

203B — SEQUENTIALLY ESTABLISH UFR IN TEST SEQUENCE UNTIL DETECTION OF LPS

203C — UPDATE SET VALUE BASED ON CURRENT UFR

(58) Field of Classification Search
      CPC ...... A61M 2205/3327; A61M 2205/50; A61M
                            2205/52; A61M 2230/205; A61M
                  2230/30; A61M 2230/42; A61M 2230/50;
                            A61M 1/3403; A61M 1/1615
      See application file for complete search history.

(56)                    References Cited

U.S. PATENT DOCUMENTS

| | | |
|---|---|---|
| 2007/0215545 A1 | 9/2007 | Bissler |
| 2010/0038317 A1 | 2/2010 | Bissler et al. |
| 2018/0043076 A1 | 2/2018 | Gerber et al. |
| 2018/0361051 A1 | 12/2018 | Kopperschmidt |

OTHER PUBLICATIONS

Written Opinion from International Patent Application No. PCT/
EP2021/054459, Mailed May 4, 2021.
Swedish Search Report; Swedish Patent Application No. 2050308-
2; Date of mailing Nov. 11, 2020 3 Pages.

ULTRAFILTRATION CONTROL IN EXTRACORPOREAL BLOOD PROCESSING

PRIORITY CLAIM

The present application is a National Phase of International Application No. PCT/EP2021/054459, filed 23 Feb. 2021, which claims priority to Swedish Application No. 2050308-2, filed 20 Mar. 2020. The entire contents of each application are incorporated herein by reference and relied upon.

TECHNICAL FIELD

The present disclosure relates generally to extracorporeal blood processing in which blood is drawn from an individual and pumped through a blood filter arrangement and back to the individual, and in particular to a control system and method for setting the rate of ultrafiltration to be achieved in the blood filter arrangement.

BACKGROUND ART

Extracorporeal blood processing is included in many extracorporeal renal replacement procedures that are commonly used to provide replacement or supplementation of an individual's natural renal function in order to remove fluid and/or waste products from the individual's blood. Such procedures ("treatment procedures") include, for example, hemodialysis, hemofiltration, hemodiafiltration, and plasmapheresis. All of these procedures involve, or may involve, extraction and removal of fluid from the blood during the processing. The extracted fluid includes plasma water and may also include some solutes dissolved in the plasma water. The extraction of fluid is commonly known as "ultrafiltration" (UF) and may be performed by establishing a pressure gradient across a porous or semi-permeable filter to drive fluid through the filter along the established pressure gradient.

Extracorporeal blood processing is performed by a dedicated apparatus based on settings which, at least partly, are entered by a caretaker or operator before start of a treatment session. It is common practice to weigh the individual before the treatment session, and compute the total amount of fluid (total UF) to be extracted and removed by subtracting an estimated "dry weight" of the individual from the current weight. The total UF and the duration of the treatment session may be entered into a control system of the apparatus, and the control system may then determine, in addition to other control parameters, a rate of fluid extraction (UF rate) to be applied by the apparatus during blood processing. The UF rate may be set to a constant value, given by the total UF divided by the duration, or be varied in accordance with a predetermined profile.

It is not uncommon that extensive fluid extraction from the individual's blood during extracorporeal blood processing causes complications in the individual, also known as intradialytic complications. One such complication is symptomatic hypotension, which involves a sudden blood pressure drop and symptoms such as cramps, nausea, vomiting and sometimes fainting. A hypotensive episode is not only strenuous for the individual, but also requires considerable attention from the staff overseeing the treatment.

One potential reason for hypotension is overestimation of the total UF for the treatment session since the individual's added weight over the dry weight need not be wholly attributable to fluid accumulation. Further, the determination of total UF does not account for the internal distribution of accumulated fluid within the individual, for example the relation between intracellular and extracellular fluid, which may have an impact on the amount of fluid that can be extracted without elevating the risk for hypotension. Still further, the individual's physiological response to fluid extraction may vary during the course of a treatment session.

Other intradialytic complications that may arise during extracorporeal blood processing, separate from hypotension, include nausea, vomiting, fever, chills, headache, cramps, chest pain, back pain, hypoglycemia, first-use syndrome, and femoral hematoma. At least some of these intradialytic complications may be at least partly attributed to fluid extraction.

There is a need for an automated technique of controlling an apparatus for extracorporeal blood processing to reduce the risk for intradialytic complications while ensuring efficient blood processing.

The prior art comprises US2007/0215545 which discloses a method of continuously optimizing the UF rate during an extracorporeal renal replacement process by receiving patient physiological condition data and UF rate data and mapping this data to a mathematical prediction model that generates a predicted status for model parameters. Depending on the predicted status, the UF rate is either increased, maintained or decreased. Thereby, the UF rate will be continuously evaluated and adjusted in real time.

Such a real-time adjustment technique is highly dependent on the accuracy and response time of the predictive model. However, the physiological response to a change in UF rate may vary between individuals, between different UF rates, between different treatment procedures, between different directions of UF rate change, etc.

SUMMARY

It is an objective to at least partly overcome one or more limitations of the prior art.

One objective is to provide a robust and automated technique of controlling an apparatus for extracorporeal blood processing to reduce the risk for intradialytic complications while ensuring efficient blood processing, at least with respect to ultrafiltration.

Another objective is to simplify the setup of an apparatus for extracorporeal blood processing.

One or more of these objectives, as well as further objectives that may appear from the description below, are at least partly achieved by a control system for an extracorporeal blood processing apparatus, an extracorporeal blood processing apparatus, a method, and a computer-readable medium, embodiments thereof being defined by the dependent claims.

A first aspect of the present disclosure is a control system for an extracorporeal blood processing apparatus. The control system comprises: logic configured to, in a treatment session, control the extracorporeal blood processing apparatus to draw blood from an individual and pump the blood through a blood filter arrangement and back to the individual while removing fluid from the blood in the blood filter arrangement in accordance with a set value for ultrafiltration rate; and an input for sensor data representing one or more physiological parameters of the individual. The logic is further configured to perform, intermittently during the treatment session, an optimization procedure to generate the set value based on the sensor data. The optimization procedure comprises: evaluating the sensor data for detection of a limiting physiological status of the individual; sequentially controlling the extracorporeal blood processing apparatus to achieve a respective ultrafiltration rate in a sequence of distinct ultrafiltration rates, until the evaluating detects the limiting physiological status for a current ultrafiltration rate; and updating the set value based on the current ultrafiltration rate for use in continuation of the treatment session subsequent to the optimization procedure.

The control system in accordance with the first aspect performs an optimization procedure that effectively controls the blood processing apparatus to sequentially step through a sequence of distinct ultrafiltration rates while monitoring the physiological response of the individual, given by the sensor data. The sequence of ultrafiltration rates thus forms a test or calibration sequence for evaluating the individual's current tolerance to the ultrafiltration rate, and to identify a proper set value for the ultrafiltration rate to prevent or reduce a negative impact on the well-being of the individual. The optimization procedure is interrupted whenever the evaluation of the sensor data detects a limiting physiological status of the individual, to thereby avoid imposing significant physiological stress on the individual. The limiting physiological status may correspond to the individual being detectably affected by the ultrafiltration rate while not yet suffering from severe symptoms such as any of the intradialytic complications discussed in the Background section.

The optimization procedure may thus be seen as an intermittent and structured test that is performed during a treatment session and that results in an updated set value to be used when the treatment session is continued after the optimization procedure. The optimization procedure may be performed at startup of the treatment session or at any time thereafter. The structured optimization procedure allows the control system to objectively determine, at any time during a treatment session, the current sensitivity of the individual to the ultrafiltration rate and generate a proper set value for the ultrafiltration rate. The control system of the first aspect thereby provides a robust, objective and automated technique of controlling extracorporeal blood processing so as to reduce the risk for intradialytic complications, by adapting the ultrafiltration rate to the individual. At the same time, since the optimization procedure explores the current upper limit for the ultrafiltration rate in relation to the individual, the control system of the first aspect may control the blood processing apparatus to achieve a high ultrafiltration rate, for example at or close to this current upper limit, to thereby ensure efficient blood processing.

In the following, various embodiments of the first aspect are defined. These embodiments provide at least some of the technical effects and advantages described in the foregoing, as well as additional technical effects and advantages as readily understood by the skilled person, e.g. in view of the following detailed description.

In some embodiments, the evaluating comprises: obtaining the sensor data for the respective ultrafiltration rate, wherein the obtaining is temporally separated by a stabilization period from initiation of the respective ultrafiltration rate at the extracorporeal blood processing apparatus.

In some embodiments, the sequence of distinct ultrafiltration rates is ordered by increasing magnitude from a minimum value.

In some embodiments, the optimization procedure further comprises, if the sensor data indicates the limiting physiological status for the minimum value, setting the set value to a predetermined value below the minimum value.

In some embodiments, the predetermined value corresponds to an ultrafiltration rate of zero.

In some embodiments, the control system is configured to perform at least two optimization procedures during the treatment session, wherein the minimum value is equal in the at least two optimization procedures.

In some embodiments, the limiting physiological status is defined to represent a non-desirable physiological status of the individual.

In some embodiments, the limiting physiological status is defined to obviate an intradialytic complication of the individual.

In some embodiments, the control system is further configured to obtain, from the sensor data, a respective initial value of the one or more physiological parameters during a calibration time period, and define the limiting physiological status as a function of the respective initial value.

In some embodiments, the calibration time period is before or at start of the treatment session.

In some embodiments, the one or more physiological parameters comprise at least one of a vital sign, a blood volume, or a cardiac output.

In some embodiments, the vital sign comprises one or more of a heart rate, a blood pressure, a blood oxygen saturation level, a respiratory rate, a skin temperature, a skin color, a urine output, a mental state, a capillary refill time, a measure of electrolyte balance in the individual, or a measure of acid-base balance in the individual.

In some embodiments, the control system is configured to autonomously initiate the optimization procedure during the treatment session.

In some embodiments, the control system is configured to initiate the optimization procedure at a predetermined time interval to a preceding optimization procedure, or as a function of the sensor data, or as a function of the set value generated by the preceding optimization procedure, or any combination thereof.

In some embodiments, the predefined time interval is smaller towards an end of the treatment session than at a beginning of the treatment session.

In some embodiments, the control system is configured to perform a series of temporally separated optimization procedures during the treatment session.

In some embodiments, the control system is further configured to receive a user-defined duration value, and set the duration of the treatment session to the user-defined duration value.

A second aspect of the present disclosure is an extracorporeal blood processing apparatus. The apparatus comprises: a pumping arrangement operable to draw blood from an individual and pump the blood through a blood filter arrangement and back to the individual while removing fluid from the blood in the blood filter arrangement at an ultrafiltration rate; and the control system of the first aspect or any of its embodiments.

A third aspect of the present disclosure is a method of operating a control system for an extracorporeal blood processing apparatus during a treatment session. The method comprises: controlling, in the treatment session, the extracorporeal blood processing apparatus to draw blood from an individual through a blood filter arrangement and pump the blood back to the individual, while removing fluid from the blood in the blood filter arrangement in accordance with a set value for ultrafiltration rate; obtaining sensor data representing one or more physiological parameters of the individual; and performing, intermittently during the treatment session, an optimization procedure to generate the set value based on the sensor data. The optimization procedure comprises: evaluating the sensor data for detection of a limiting physiological status of the individual; sequentially controlling the extracorporeal blood processing apparatus to achieve a respective ultrafiltration rate in a sequence of distinct ultrafiltration rates, until the evaluating detects the limiting physiological status for a current ultrafiltration rate; and updating the set value based on the current ultrafiltration rate for use in continuation of the treatment session subsequent to the optimization procedure.

Any one of the embodiments of the first aspect may be adapted and implemented as an embodiment of the third aspect.

A fourth aspect of the invention is a computer-readable medium comprising computer instructions which, when executed by one or more processors, cause the one or more processors to perform the method of the third aspect and any of its embodiments.

Still other objectives, features, embodiments, aspects and advantages may appear from the following detailed description, from the attached claims as well as from the drawings.

BRIEF DESCRIPTION OF THE DRAWINGS

Embodiments will now be described in more detail with reference to the accompanying drawings.

DETAILED DESCRIPTION OF EXAMPLE EMBODIMENTS

Figures 1, 2:
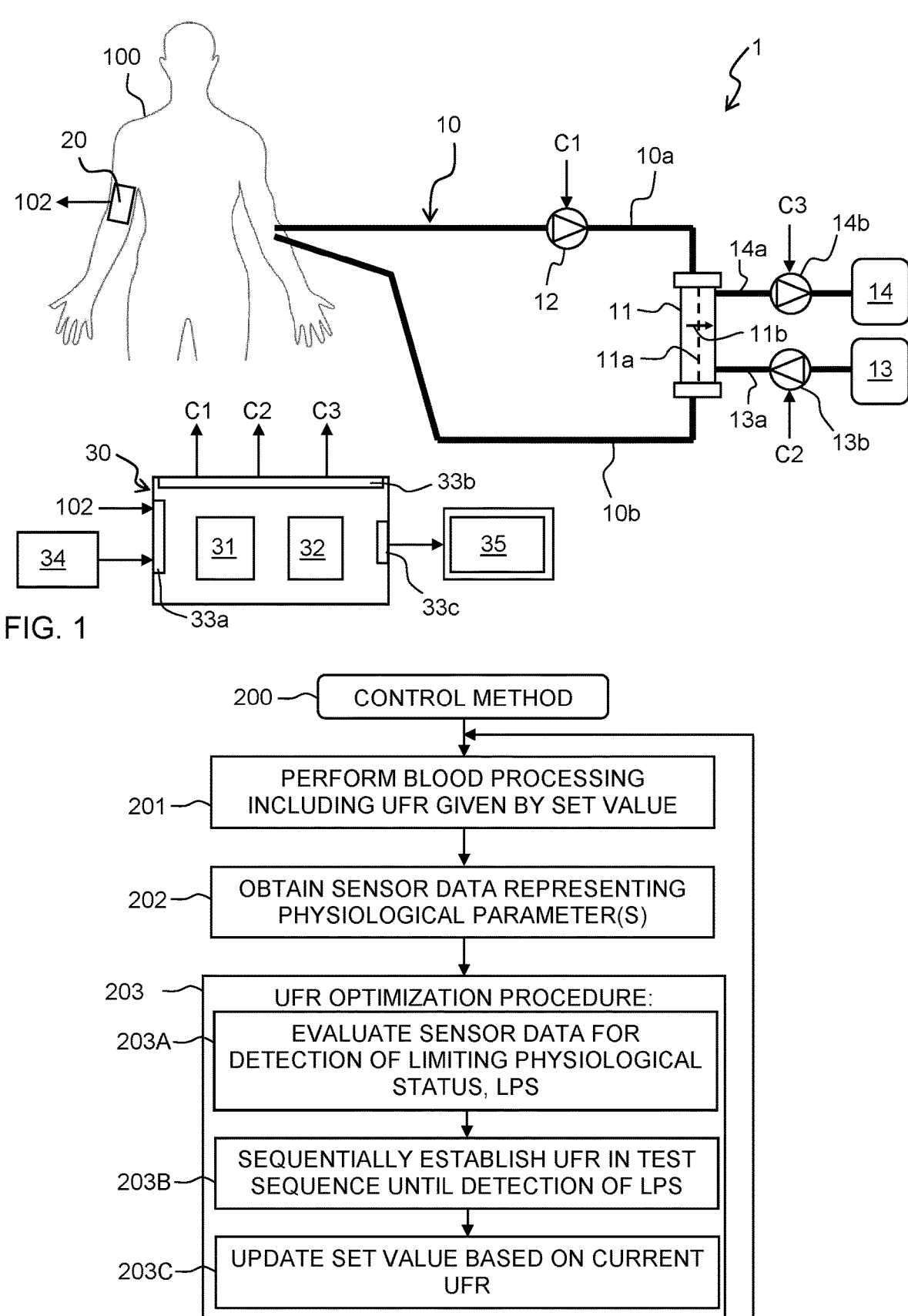
FIG. 1 is a schematic overview of an example blood processing apparatus connected to a human individual.
FIG. 2 is a flow chart of an example control method in accordance with an embodiment.

Embodiments will now be described more fully hereinafter with reference to the accompanying drawings, in which some, but not all, embodiments are shown. Indeed, the subject of the present disclosure may be embodied in many different forms and should not be construed as limited to the embodiments set forth herein; rather, these embodiments are provided so that this disclosure may satisfy applicable legal requirements.

Also, it will be understood that, where possible, any of the advantages, features, functions, devices, and/or operational aspects of any of the embodiments described and/or contemplated herein may be included in any of the other embodiments described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more", even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments. The term "and/or" includes any and all combinations of one or more of the associated listed items.

It will furthermore be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing the scope of the present disclosure.

Well-known functions or constructions may not be described in detail for brevity and/or clarity. Unless otherwise defined, all terms (including technical and scientific terms) used herein have the same meaning as commonly understood by one of ordinary skill in the art to which this disclosure belongs.

Like reference signs refer to like elements throughout.

Embodiments relate to a technique of controlling ultrafiltration during extracorporeal blood processing. As used herein, "extracorporeal blood processing" refers to a technique of extracting blood from an individual, which may be a human or an animal, processing the blood outside the body of the individual to at least remove fluid from the blood, and returning the processed blood to the individual. Embodiments are applicable to any apparatus that is operable to perform such extracorporeal blood processing, for example as part of extracorporeal renal replacement therapy, including without limitation hemodialysis (HD), hemofiltration (HF), and hemodiafiltration (HDF), or for supportive fluid removal between HD, HF or HDF sessions, or as an adjunctive therapy for patients with congestive heart failure (CHF).

FIG. 1 illustrates an embodiment of an apparatus or system 1 for hemodialysis 1. The apparatus 1 comprises an extracorporeal blood circuit 10 and a treatment fluid circuit, which are interfaced by a blood filtration unit 11. The blood filtration unit 11 defines a blood side and a treatment fluid side separated by a porous or semipermeable membrane 11a. The filtration unit 11 may be any well-known dialyzer useful for hemodialysis, such as a coil dialyzer, a parallel plate dialyzer, a hollow fiber dialyzer, etc. Generally, the apparatus 1 may comprise any number of blood filtration units, which collectively define a "blood filtration arrangement". The blood circuit 10 defines a blood extraction path or line 10a and a blood return path or line 10b, which are connected to the blood side of the filtration unit 11. The blood circuit 10 is connected in fluid communication with the blood system of an individual 100 by any conventional device, such as needles or catheters. One or more pumps 12 (one shown) are arranged in the blood circuit 10 and operable to draw blood from the individual 100 and pump the blood through the blood side of the filtration unit 11 and back to the individual 100. The blood pump 12 may be a peristaltic pump or any other suitable pump. The treatment fluid circuit comprises a source 13 of fresh treatment fluid and a receptacle or drain 14 for effluent fluid. The effluent fluid comprises spent treatment fluid and fluid ("ultrafiltrate") extracted from the blood. The treatment fluid circuit includes an arrangement of fluid lines that define an inlet conduit 13a connected to an inlet on the treatment fluid side of the filtration unit 11, and an outlet conduit 14a connected to an outlet on the treatment fluid side of the filtration unit 11. A first pump 13b ("supply pump") is arranged in the inlet conduit 13a to pump treatment fluid from the source 13, and a second pump 14b ("effluent pump") is arranged in the outlet conduit 14a to pump effluent fluid towards the receptacle 14. The pumps 14a, 14b may be peristaltic pumps or pumps of any other suitable type.

The operation of the pumps 12, 14a, 14b is controlled by control signals C1, C2, C3 generated by a control system 30.

The pumps 12, 14a, 14b may be collectively designated as a "pumping arrangement", which is controlled to achieve ultrafiltration of the blood in the filtration unit 11 as well as, in the illustrated example, dialysis treatment of the blood. Specifically, the pumping arrangement may be operated to establish a pressure gradient across the membrane 11a to drive fluid through the membrane 11a, as indicated by arrow 11b. It understood that FIG. 1 is merely given as an example. For example, in an apparatus that is configured to only perform ultrafiltration, the source 13, the inlet conduit 13a and the supply pump 13b may be omitted.

In the illustrated embodiment, the control system 30 comprises one or more processors 31 (one shown) and computer memory 32. A control program may be stored in the memory 32 and executed by the processor(s) 31 to perform any of the methods, functions or procedures described herein. The control program in combination with the processor(s) 31 and the memory 32 define "logic" of the control system 30. The control program may be supplied to the control system 30 on a computer-readable medium, which may be a tangible (non-transitory) product (e.g. magnetic medium, optical disk, read-only memory, flash memory, etc.) or a propagating signal. In an alternative embodiment, the control system 30 is configured with logic that consists of hardware components.

The control system 30 further comprises an input interface 33a for connection to one or more sensor devices 20 (one shown) associated with the individual 100. The respective sensor device 20 is configured to provide sensor data 102 representative of one or more physiological parameters of the individual 100. As indicated, the input interface 33a may also be configured for connection to one or more input devices 34 (one shown) that enable a user ("operator") to supply input data. For example, the input device(s) 34 may comprise a keyboard, keypad, computer mouse, control button, touch screen, etc. Although not shown in FIG. 1, the input interface 33a may be further configured to receive input signals from the apparatus 1, such as signals from various sensors, status signals, error signals, control signals, alerts, etc. The control system 30 further comprises a first output interface 33b for providing the control signals C1, C2, C3 to the pumping arrangement, and a second output interface 33c for connection to one or more output devices 35 (one shown), for example for providing information to the operator. For example, the output device(s) 35 may comprise a display device, an indicator lamp, an alarm device, a speaker, a printer, etc. The interfaces 33a, 33b, 33c may be configured for wired or wireless connection.

It is understood that only components relevant to the following description are represented in FIG. 1. Other potential components of the apparatus 1 are well within the purview of one skilled in the art to ascertain, such as clamps, valves, sensors (flow rate, conductivity, pressure, air, blood, etc.), drip chambers, pumps, heaters, filters, etc.

The apparatus 1 is operated by the control system 30 to perform a treatment session, which is a coherent time period during which the individual 100 is connected to the apparatus 1 and subjected to extracorporeal blood processing for the purpose of achieving a specific therapeutic objective, for example to attain a prescribed dose target and/or a desired physiological status of the individual 100. Before the treatment session is started, a caretaker or other operator may enter control data for the treatment session, for example by use of the input device(s) 34. The control data may include the duration of the treatment session, treatment fluid composition, treatment fluid flow rate, blood flow rate, type of filtration unit 11, etc, as well as threshold values and/or limits to be applied during the treatment session. Conventionally, as described in the Background section, the control data also includes the total fluid to be removed from the blood of the individual 100 during the treatment session ("total UF"). However, in at least some of the embodiments described herein, the total UF need not be entered.

FIG. 2 is a flow chart of a control method 200 that may be performed by the control system 30 during a treatment session in accordance with an embodiment. In step 201, the apparatus 1 is operated to perform extracorporeal blood processing while removing fluid from the blood at an ultrafiltration rate (denoted UFR in the following) The UFR designates the amount of fluid removed from the blood per unit time and is given by a UFR set value. In step 202, which may be performed continuously during the method 200, or at least during an optimization procedure in step 203, the sensor data 102 is obtained from the sensor device(s) 20 associated with the individual 100 (FIG. 1). The optimization procedure in step 203 is configured to update the UFR set value and involves steps 203A-203C. In step 203A, the sensor data 102 is evaluated for detection of a limiting physiological status (denoted LPS in the following). Step 203B is performed concurrently with step 203A and operates the apparatus 1 to achieve different UFRs according to a test sequence of distinct UFRs. Step 203B is stopped whenever step 203A detects the LPS. At this time, step 203B thus operates the apparatus 1 at a current UFR that results in the LPS. In step 203C, the UFR set value is updated based on the current UFR. Depending on implementation, step 203C may involve updating the UFR set value so as to operate the apparatus 1 either at the current UFR, or with a predefined relation (above/below) to the current UFR. Following step 203, the control method proceeds to step 201, in which the apparatus 1 is operated at the updated UFR set value.

The optimization procedure 203 is performed to evaluate the individual's current tolerance to ultrafiltration and to identify a proper UFR set value to prevent or reduce a negative impact on the well-being of the individual 100, where the onset of the negative impact is represented by the LPS.

It is realized that the control method 200, by way of the optimization procedure 203, is capable of reducing the risk for intradialytic complications while ensuring efficient blood processing.

In some embodiments, the LPS may be defined to represent a non-desirable physiological status of the individual 100 and/or be defined to obviate an intradialytic complication of the individual 100.

In some embodiments, the optimization procedure 203 may be implemented to systematically find the current maximum UFR that maintains the well-being of the individual. This may be achieved by using a test sequence of UFRs that are ordered by increasing magnitude. Thus, step 203B may involve a stepwise increase in the UFR, starting from a minimum UFR and ending when a current UFR results in the LPS. Thereby, the optimization procedure 203 will consistently test the individual's response to a gradual increase of the UFR, which will eliminate the impact of any hysteresis in the individual's response, for example that the individual responds differently to an increase and a decrease in UFR by the same amount.

As understood from the example in FIG. 2, the optimization procedure 203 may be performed more than once during a treatment session. Thus, in some embodiments, the control method 200 performs a series of temporally separated optimization procedures 203 during a treatment session. Thereby, the UFR will be intermittently adjusted to the physiological response of the individual 100. Since the individual's tolerance to UFR may change as the treatment session progresses, this will further reduce the risk of intradialytic complications.

In some embodiments, the test sequence is predefined. In other embodiments, the test sequence is dynamically determined, for example as a function of the sensor data 102 and/or the time from start of the treatment session and/or one or more previous UFR set values generated by the optimization procedure 203. For example, the change in UFR between consecutive time steps in the test sequence may be decreased subsequent to one or more time points during the treatment session. Such a time point may, for example, be a specific time during the treatment session, or be identified when one or more of the UFR set values fulfil a predefined criterion, such as when a UFR set value falls below or exceeds a designated threshold or when consecutive UFR set values follow a designated trend.

In one embodiment, all the test sequences of the optimization procedures 203 start from the same minimum UFR ($UFR_M$). This will ensure consistency in the operation of the control method 200.

In some embodiments, step 203C updates the UFR set value to a predetermined "UFR termination value" when step 203B detects the LPS for $UFR_M$. The UFR termination value results in an UFR below $UFR_M$, for example an UFR of zero or close to zero. When the LPS is detected already at the onset of the optimization procedure, this may be an indication that the individual has reached or is approaching its dry weight and that ultrafiltration should be terminated or at least significantly reduced for the remainder of the treatment session. Such embodiments enable fully automated control of the ultrafiltration during the treatment session and obviate the need for the caretaker to estimate and enter the total UF before the treatment session. These embodiments thereby have the potential of improving the individual's well-being as well as facilitating the task of the caretaker.

Figures 3A, 3B, 3C:
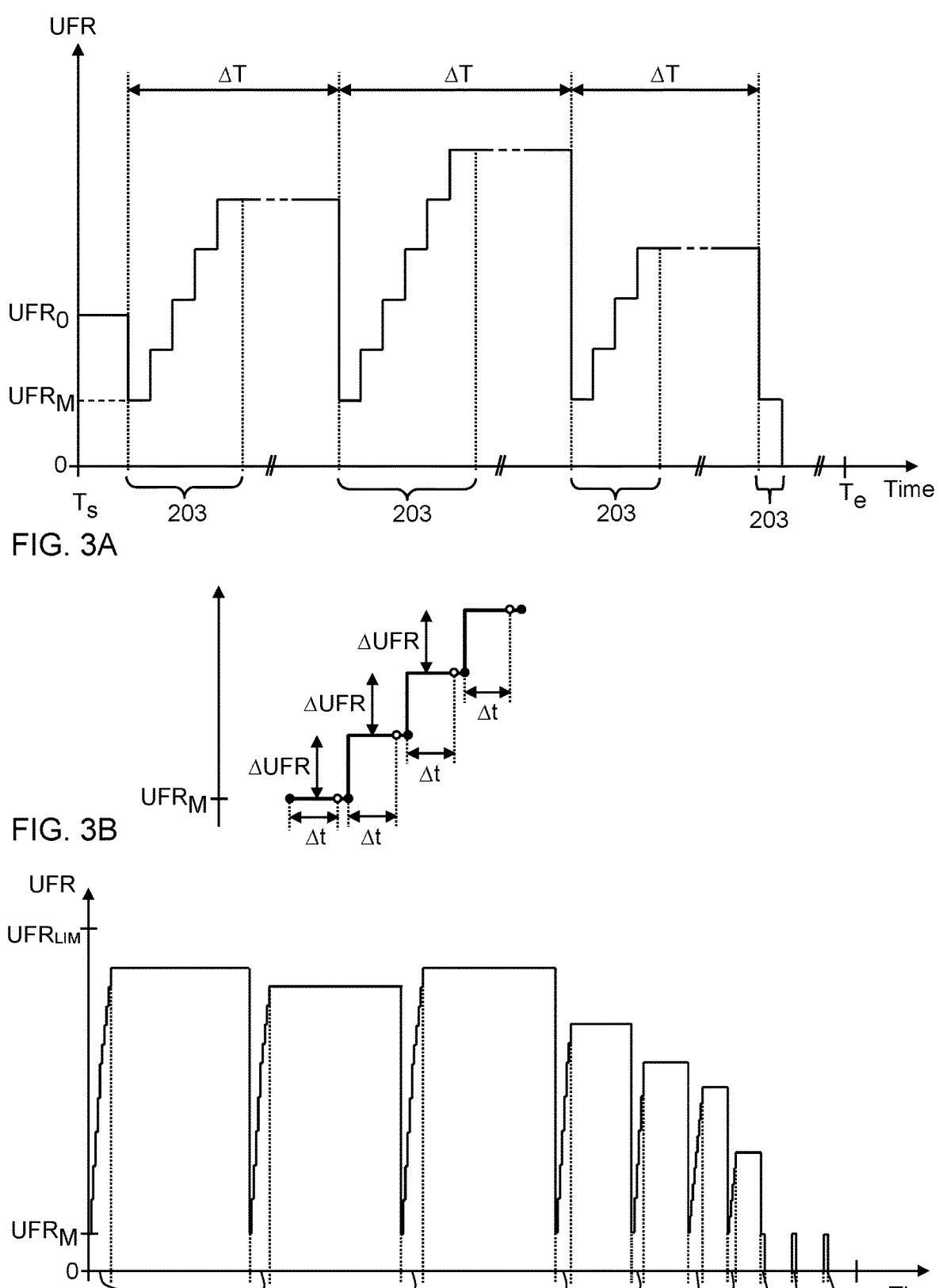
FIGS. 3A-3C are graphs of ultrafiltration rate as a function of time during example treatment sessions performed by a blood processing apparatus subject to the control method of FIG. 2.

The foregoing embodiments are further exemplified in FIGS. 3A-3C, which are graphs of UFR generated by a blood processing apparatus 1 during a treatment session by use of the control method 200 in FIG. 2.

In FIG. 3A, a treatment session starts at time Ts and ends at time Te. As noted above, Te may be entered by the caretaker as part of the control data. At start of treatment, the method 200 controls the apparatus 1 to generate an initial ultrafiltration rate $UFR_0$. In one example, $UFR_0$ is a pre-stored value which may be specific to the individual 100 or generic for a group of individuals. In another example, $UFR_0$ is determined by the method 200 based on one or more preceding treatment sessions, for example as function of an average, median or maximum UFR attained during the preceding treatment session(s). In yet another example, $UFR_0$ is entered by the caretaker in preparation of the treatment session, for example as part of the control data. In the illustrated example, the method 200 performs four optimization procedures 203 separated by a respective time interval $\Delta T$. Each of the optimization procedures evaluates, by steps 203A-203B, a test sequence of stepwise increasing UFRs as seen in FIG. 3A. In the illustrated example, when step 203B detects the LPS for a current UFR in the test sequence, the UFR set value is updated to operate the apparatus 1 at this current UFR until a subsequent optimization procedure is initiated or the treatment session is terminated at time Te. In the illustrated example, the test sequence starts from the same minimum ultrafiltration rate, $UFR_M$, in all optimization procedures 203. As seen, the different optimization procedures 203 may result in different UFR set values. In the last optimization procedure in FIG. 3A, the UFR is set to zero since the LPS is detected for the $UFR_M$, and ultrafiltration is thus automatically terminated.

FIG. 3B shows an example of a test sequence of UFRs generated by the optimization procedure 203. The test sequence starts at $UFR_M$ and increases the ultrafiltration rate in steps of magnitude $\Delta UFR$. In some embodiments, the step-increase $\Delta UFR$ is given by a fixed value. Thus, the ultrafiltration may be increased by a fixed absolute amount between steps (as shown), or by a fixed relative value, for example a percentage. However, it is conceivable to otherwise vary the step-increase $\Delta UFR$ during the optimization procedure 203. For example, the step-increase $\Delta UFR$ may be decreased when the ultrafiltration rate exceeds a predetermined threshold. This will reduce the risk that the test sequence results in an ultrafiltration rate that impairs the well-being of the individual.

In the example of FIG. 3B, filled dots indicate a first time point at which the optimization procedure changes the UFR in accordance with the test sequence, and open dots indicate a second time point at which the sensor data is obtained and evaluated for detection of the LPS. Thus, the first and second time points are separated by a time period $\Delta t$ that allows that the individual 100 to respond to the changed UFR. This "stabilization period" At will improve the effectiveness of the method 200 in ensuring the well-being of the individual and obviating intradialytic complications. In one example, the stabilization period is in the range of 10-90 seconds, and the maximum duration of the optimization procedure 203 is in the range of 1-10 minutes.

FIG. 3C is a graph of another example of UFR as a function of time during a treatment session performed under control of the method 200. In the illustrated example, the temporal separation of optimization periods 203 (cf. time interval $\Delta T$ in FIG. 3A) varies during the treatment session. Specifically, the temporal separation is smaller towards the end of the treatment session. This may be advantageous since the individual is expected to exhibit an increased sensitivity to ultrafiltration as its body is being depleted of excess fluid. In some embodiments, the time interval $\Delta T$ is predefined and may thus be predefined to vary as a function of time, for example in relation to the start time Ts. In some embodiments, the control method autonomously initiates the optimization procedure 203 during the treatment session. Thus, rather than being predetermined, the time interval $\Delta T$ is determined dynamically by the control method 200. In some embodiments, the time interval is $\Delta T$ determined dynamically as a function of the sensor data 102. For example, the control method 200 may initiate the optimization procedure 203 whenever the sensor data 102 fulfils a predefined criterion. The predefined criterion may be the LPS or any other physiological status of the individual. In some embodiments, the time interval $\Delta T$ is determined as a function of the UFR set value, i.e. the UFR set value determined by step 203C of the latest optimization procedure 203. For example, if the UFR set value falls below a predefined threshold, the time interval $\Delta T$ may be decreased to a predefined value or by a predefined absolute or relative amount. The control method 200 may also apply any combination of the foregoing embodiments to determine the time interval $\Delta T$.

FIG. 3C also shows that the UFR is set to the UFR termination value when the LPS is detected for $UFR_M$, which typically occurs towards the end of the treatment session. In the illustrated example, the method continues to repeatedly initiate the optimization procedure 203 after setting the UFR termination value, to ensure that the control method is capable of again increasing the UFR if the individual is found to sustain further ultrafiltration.

In some embodiments, the control method may automatically terminate the treatment session when the LPS is detected for $UFR_M$ in one or more optimization procedures 203. Thus, the treatment session is not terminated at a predetermined time point Te in relation the start time Ts, but when the individual is deemed to have reached the dry weight based on the sensor data 102. Such embodiments are, for example, applicable when the blood processing apparatus 1 is configured to only perform ultrafiltration.

FIG. 3C also indicates an upper UFR limit, $UFR_{LIM}$. In some embodiments, the upper UFR limit defines the maximum UFR that may be generated by the test sequence. It is also conceivable that the control method 200 is caused to interrupt the treatment session and/or generate an alert or alarm signal (for example, on the output device(s) 35 in FIG. 1) whenever the generated UFR reaches $UFR_{LIM}$.

Reverting to FIG. 2, step 203A may detect the limiting physiological status (LPS) based on a single physiological parameter or a combination of physiological parameters of the individual 100 as represented in the sensor data 102. In the context of the present disclosure, the term "physiological parameter" denotes any physiology-related quantity that may be monitored to determine one or more quantitative physiological levels associated with an individual. In some embodiments, the LPS is detected based on at least one of a blood volume, a cardiac output or a vital sign. The blood volume is the total volume of blood in the circulatory system of the individual 100. For example, changes in blood volume (also known as relative blood volume, RBV) may be measured online by commercially available equipment. As used herein, blood volume is also intended to comprise hematocrit. The cardiac output is the volume of blood being pumped by the heart of the individual per unit time. Several techniques are available to measure cardiac output, for example doppler ultrasound, analysis of systolic and diastolic blood pressures, impedance cardiography, electrical cardiometry, ultrasound dilution, etc. The vital sign may comprise any physiological parameter that is routinely monitored by medical professionals and health care providers such as a skin (body) temperature, heart rate (pulse rate), a respiratory rate (breathing rate), or blood pressure. Alternatively or additionally, the vital sign may comprise one or more of a blood oxygen saturation level, a skin color, a urine output, a mental state, a capillary refill time, a measure of the electrolyte balance in the individual, and a measure of the acid-base balance in the individual.

Step 203B may detect the LPS by operating a predefined evaluation function on the physiological parameter(s) and evaluating the result in relation to an evaluation criterion. The evaluation function may operate on an absolute value of the respective physiological parameter and/or a relative change in the respective physiological parameter. In some embodiments, the LPS may additionally be detected based on one or more operating parameters of the blood processing apparatus, for example a pressure measured in the return path 10a and/or the extraction path 10b. In a non-limiting example, the evaluation function is a function of at least blood volume and heart rate.

In some embodiments, the LPS is predefined, for example in terms of the above-mentioned evaluation criterion.

In some embodiments, the control method 200 instead comprises a calibration step which is performed during a calibration time period. The calibration step may comprise obtaining a respective initial value of the one or more physiological parameters from the sensor data 102, and defining the LPS as a function of the respective initial value. For example, the calibration step may determine the above-mentioned evaluation criterion based on the initial values.

In some embodiments, the calibration step is performed before or at the start of the treatment session, so that the initial values represent the physiological status of the individual as unaffected by ultrafiltration.

Figure 4:
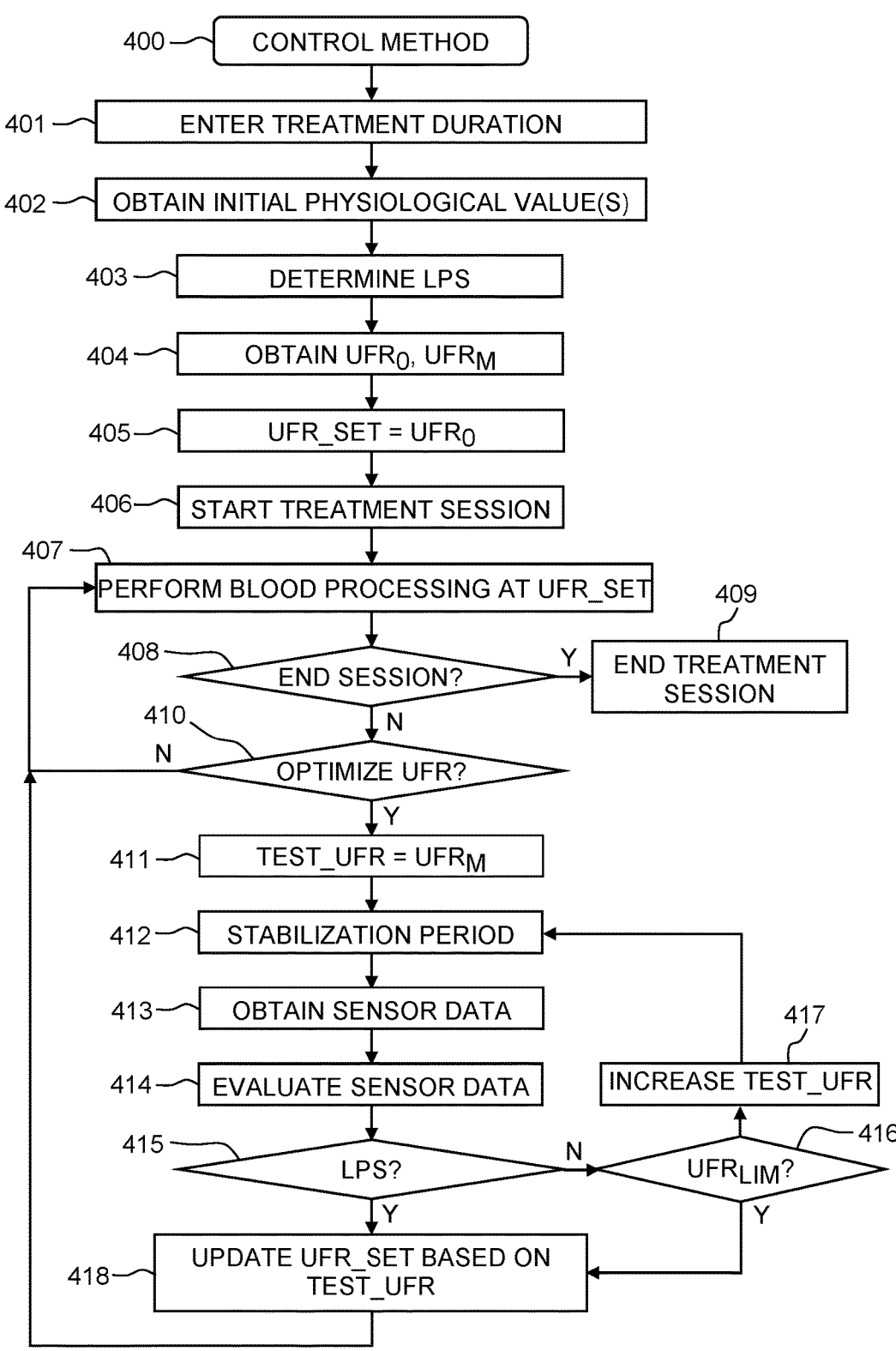
FIG. 4 is a flow chart of a detailed example of a control method in accordance with embodiments.

FIG. 4 is a flow chart of a control method 400, which is an example implementation of the control method 200 in FIG. 2. In step 401, the treatment duration is entered by the caretaker via the input device(s) 34 (FIG. 1). Based on the treatment duration, the control method 400 is capable of determining the end time Te when the start time Ts is known. Although not shown in FIG. 4, step 401 may include the caretaker entering further control data, as described hereinabove. Steps 402-403 correspond to the above-mentioned calibration step. In step 402, a respective initial value of the physiological parameter(s) is obtained from the sensor data 102. In step 403, the LPS is defined based on the initial value(s). For example, step 403 may comprise determining the above-mentioned evaluation criterion. In step 404, the initial UFR ($UFR_0$) and the minimum UFR ($UFR_M$) are determined, for example as described hereinabove. In step 405, the UFR set value (UFR_SET) is set to $UFR_0$. Step 406 operates the blood processing apparatus to start the treatment session, and step 407 controls the blood processing apparatus to continuously achieve an ultrafiltration rate given by UFR_SET. Step 408 may check if the treatment session should be terminated, for example in the event of an alarm condition, error detection or if the end time Te has been reached. If the treatment session should be terminated, step 408 proceeds to step 409. Otherwise, step 408 proceeds to step 410, which evaluates if the optimization procedure should be initiated, for example in accordance with any of the embodiments for determining $\Delta T$ as described hereinabove. If the optimization procedure should not be initiated, the ultrafiltration continues without change. Otherwise, step 410 proceeds to perform the optimization procedure, implemented by steps 411-418. In step 411, a UFR control parameter (TEST_UFR) is set to $UFR_M$, and one or more of the control signals C1-C3 to the pumping arrangement is modified to result in a corresponding UFR (FIG. 1). Step 412 causes the method to wait during the stabilization period ($\Delta t$ in FIG. 3B) before proceeding to step 413, in which a respective current value of the physiological parameter(s) is obtained from the sensor data 102 (FIG. 1). Step 414 evaluates the current value(s) for detection of the LPS, for example by use of the above-mentioned evaluation function. If the LPS is not detected, step 415 proceeds to step 416 which checks if TEST_UFR is at the upper UFR limit, ($UFR_{LIM}$). If not, step 416 proceeds to step 417 which increases TEST_UFR by $\Delta UFR$ (FIG. 3B), for example as described hereinabove, and proceeds to step 412. If step 415 detects the LPS, the method proceeds to step 418 which updates UFR_SET based on TEST_UFR and proceeds to step 407, which controls the blood processing apparatus to continuously achieve an ultrafiltration rate given by the updated UFR_SET. Likewise, if step 416 determines that TEST_UFR is at the upper UFR limit, the method proceeds to step 418.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

Further, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

The invention claimed is:

1. A control system for an extracorporeal blood processing apparatus, said control system comprising:

one or more processors and a computer-readable medium including computer logic which, when executed by the one or more processors during a treatment session, controls the extracorporeal blood processing apparatus to draw blood from an individual and pump the blood through a blood filter arrangement and back to the individual while removing fluid from the blood in the blood filter arrangement in accordance with a set value for an ultrafiltration rate, and to input sensor data representing one or more physiological parameters of the individual, wherein the computer logic is further configured to perform, intermittently during the treatment session, an optimization procedure to generate the set value based on the sensor data, the optimization procedure comprising:

evaluating the sensor data for detection of a limiting physiological status (LPS) of the individual, sequentially controlling the extracorporeal blood processing apparatus to achieve a respective ultrafiltration rate in a sequence of distinct ultrafiltration rates, until the evaluating detects the limiting physiological status (LPS) for a current ultrafiltration rate, and updating the set value based on the current ultrafiltration rate for use in continuing the treatment session subsequent to the optimization procedure, wherein the evaluating comprises obtaining the sensor data for the respective ultrafiltration rate, wherein the obtaining is temporally separated by a stabilization period ($\Delta t$) from initiation of the respective ultrafiltration rate at the extracorporeal blood processing apparatus, and wherein the sequence of distinct ultrafiltration rates is ordered by increasing magnitude from a minimum value ($UFR_M$), wherein the control system is configured to perform at least two optimization procedures during the treatment session, and wherein the minimum value ($UFR_M$) is equal in the at least two optimization procedures, and wherein after the at least two optimization procedures are performed, additional optimization procedures are performed where the ultrafiltration rate is increased.

2. The control system of claim 1, wherein the optimization procedure further comprises, if the sensor data indicates the limiting physiological status (LPS) for the minimum value ($UFR_M$), updating the set value to a predetermined value below the minimum value ($UFR_M$).

3. The control system of claim 2, wherein the predetermined value corresponds to an ultrafiltration rate of zero.

4. The control system of claim 1, wherein the limiting physiological status (LPS) is defined to represent a non-desirable physiological status of the individual.

5. The control system of claim 1, wherein the limiting physiological status (LPS) is defined to obviate an intradialytic complication of the individual.

6. The control system of claim 1, which is further configured to obtain, from the sensor data, a respective initial value of the one or more physiological parameters during a calibration time period, and define the limiting physiological status (LPS) as a function of the respective initial value.

7. The control system of claim 6, wherein the calibration time period is before or at start of the treatment session.

8. The control system of claim 1, wherein the one or more physiological parameters comprise at least one of a vital sign, a blood volume, or a cardiac output.

9. The control system of claim 8, wherein the vital sign comprises one or more of a heart rate, a blood pressure, a blood oxygen saturation level, a respiratory rate, a skin temperature, a skin color, a urine output, a mental state, a capillary refill time, a measure of electrolyte balance in the individual, or a measure of acid-base balance in the individual.

10. The control system of claim 1, which is configured to autonomously initiate the optimization procedure during the treatment session.

11. The control system of claim 1, which is configured to initiate the optimization procedure at a predetermined time interval ($\Delta T$) to a preceding optimization procedure, or as a function of the sensor data, or as a function of the set value generated by the preceding optimization procedure, or any combination thereof.

12. The control system of claim 11, wherein the predetermined time interval ($\Delta T$) is smaller towards an end of the treatment session than at a beginning of the treatment session.

13. The control system of claim 1, which is configured to perform a series of temporally separated optimization procedures during the treatment session.

14. The control system of claim 1, which is further configured to receive a user-defined duration value, and set the duration of the treatment session to the user-defined duration value.

15. An extracorporeal blood processing apparatus comprising:

a pumping arrangement operable to draw blood from an individual and pump the blood through a blood filter arrangement and back to the individual while removing fluid from the blood in the blood filter arrangement at an ultrafiltration rate; and a control system comprising:

one or more processors and a computer-readable medium including computer logic which, when executed by the one or more processors during a treatment session, controls the pumping arrangement to draw blood from the individual and pump the blood through the blood filter arrangement and back to the individual while removing fluid from the blood in the blood filter arrangement in accordance with a set value for the ultrafiltration rate, and to input sensor data representing one or more physiological parameters of the individual, wherein the computer logic is further configured to perform, intermittently during the treatment session, an optimization procedure to generate the set value based on the sensor data, the optimization procedure comprising:

evaluating the sensor data for detection of a limiting physiological status (LPS) of the individual, sequentially controlling the pumping arrangement to achieve a respective ultrafiltration rate in a sequence of distinct ultrafiltration rates, until the evaluating detects the limiting physiological status (LPS) for a current ultrafiltration rate, and updating the set value based on the current ultrafiltration rate for use in continuing the treatment session subsequent to the optimization procedure, wherein the evaluating comprises obtaining the sensor data for the respective ultrafiltration rate, wherein the obtaining is temporally separated by a stabilization period ($\Delta t$) from initiation of the respective ultrafiltration rate at the extracorporeal blood processing apparatus, and wherein the sequence of distinct ultrafiltration rates is ordered by increasing magnitude from a minimum value ($UFR_M$), wherein the control system is configured to perform at least two optimization procedures during the treatment session, and wherein the minimum value ($UFR_M$) is equal in the at least two optimization procedures, and wherein after the at least two optimization procedures are performed, additional optimization procedures are performed where the ultrafiltration rate is increased.

16. A method of operating a control system for an extracorporeal blood processing apparatus during a treatment session which is performed via instructions stored on a computer-readable medium, wherein the instructions are executed by one or more processors, the method comprising:

controlling, in the treatment session, the extracorporeal blood processing apparatus to draw blood from an individual through a blood filter arrangement and pump the blood back to the individual, while removing fluid from the blood in the blood filter arrangement in accordance with a set value for an ultrafiltration rate;

obtaining sensor data representing one or more physiological parameters of the individual; and performing, intermittently during the treatment session, an optimization procedure to generate the set value based on the sensor data;

wherein the optimization procedure comprises:

evaluating the sensor data for detection of a limiting physiological status of the individual;

sequentially controlling the extracorporeal blood processing apparatus to achieve a respective ultrafiltration rate in a sequence of distinct ultrafiltration rates, until the evaluating detects the limiting physiological status for a current ultrafiltration rate; and updating the set value based on the current ultrafiltration rate for use in continuing the treatment session subsequent to the optimization procedure, wherein the evaluating comprises obtaining the sensor data for the respective ultrafiltration rate, wherein the obtaining is temporally separated by a stabilization period ($\Delta t$) from initiation of the respective ultrafiltration rate at the extracorporeal blood processing apparatus, and wherein the sequence of distinct ultrafiltration rates is ordered by increasing magnitude from a minimum value ($UFR_M$), wherein the control system is configured to perform at least two optimization procedures during the treatment session, and wherein the minimum value ($UFR_M$) is equal in the at least two optimization procedures, and wherein after the at least two optimization procedures are performed, additional optimization procedures are performed where the ultrafiltration rate is increased.

* * * * *